United States Patent [19]

de Sousa et al.

[11] Patent Number: 4,503,100
[45] Date of Patent: Mar. 5, 1985

[54] MOTHPROOFING AND BEETLEPROOFING AGENT FOR KERATINOUS MATERIAL AND PROCESS

[75] Inventors: Bernardo de Sousa; Werner Schmid, both of Riehen; Klaus Artz, Muttenz, all of Switzerland

[73] Assignee: Ciba-Geigy Corporation, Ardsley, N.Y.

[21] Appl. No.: 523,485

[22] Filed: Aug. 15, 1983

[30] Foreign Application Priority Data

Aug. 26, 1982 [CH] Switzerland ................. 5081/82

[51] Int. Cl.$^3$ .............................................. A23F 3/34
[52] U.S. Cl. ....................................... 427/428; 8/490; 252/8.6; 252/8.7; 252/8.8; 252/8.9; 514/271
[58] Field of Search .............. 424/189, 186, 187, 254; 252/8.6, 8.8, 8.7, 8.9; 427/389.9, 392, 389, 428; 8/490

[56] References Cited

U.S. PATENT DOCUMENTS 4,239,762  12/1980  Kramer et al. .
4,283,444   8/1981  de Sousa et al. ................. 427/421

OTHER PUBLICATIONS

Journal of the Textile Institute, vol. 67, (1976).

*Primary Examiner*—Bernard D. Pianalto
*Attorney, Agent, or Firm*—Edward M. Roberts

[57] ABSTRACT

A composition for protecting keratin material, in particular woolen textiles, against attack by keratin pests, in particular moth and beetle larvae, which contains a specifically substituted 5-phenylcarbamoylbarbituric acid or a salt thereof and a synthetic pyrethroid as the active compound combination, is described, as well as a process, using the said active compound combination, for imparting a finish to the said material against attack by keratin pests.

21 Claims, No Drawings

MOTHPROOFING AND BEETLEPROOFING AGENT FOR KERATINOUS MATERIAL AND PROCESS

The present invention relates to an agent for protecting keratin material against attack by keratin-consuming pests, in particular an agent for protecting wool, furs and feathers against attack, and damage caused by eating, by moth and beetle larvae, and also a process for protecting the said materials against attack by keratin-consuming pests.

It is known that certain synthetic pyrethroids can be used for controlling keratin-consuming pests. See, for example, J. Text. Inst. 1976, No. 3, Vol. 67, pages 77 to 81 German Offenlegungsschrift No. 2,923,217; U.S. Pat. No. 4,219,593 and European Pat. No. 11,789. These pyrethroids have a very good action against moth larvae, while their action against the larvae of fur beetles and carpet beetles is less pronounced. It is also known from U.S. Pat. No. 4,283,444 that certain 5-phenylcarbamoylbarbituric acids can also be employed for controlling keratin pests. These acids have a particularly good action against fur beetle and carpet beetle larvae. U.S. Pat. No. 4,283,444 also describes agents containing a combination of the said synthetic pyrethroids and 5-phenylcarbamoylbarbituric acids, by means of which it is possible to protect keratin materials (for example wool) in an excellent manner against attack by keratin pests.

It has now been found, surprisingly, that a very particularly high protective action against the said pests can be achieved on keratin materials, in particular wool, by means of a composition (a combination preparation) containing a synthetic pyrethroid and a 5-phenylcarbamoylbarbiturate which has specific substituents in the phenyl ring or that smaller quantities of the combination of active compounds are required for the same protective action than when using the known compositions mentioned above.

The composition according to the invention contains (A) one or more 5-phenylcarbamoylbarbiturate(s) of the formula

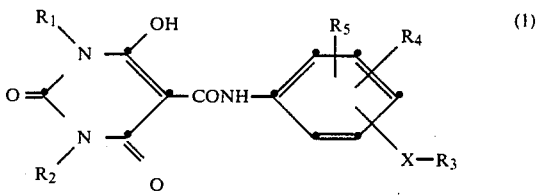

or tautomeric forms or salts thereof, in which $R_1$ and $R_2$ independently of one another are $C_1$-$C_4$-alkyl, $C_3$-$C_6$-cycloalkyl, $C_2$-$C_4$-alkenyl, benzyl, phenyl, or phenyl which is substituted by 1 to 3 substituents belonging to the group comprising halogen, $C_1$-$C_4$-alkyl, $C_1$-$C_4$-alkoxy and nitro, $R_3$ is $C_1$-$C_4$-halogenoalkyl, phenyl or phenyl which is substituted by 1–3 substituents belonging to the group comprising $C_1$-$C_4$-halogenoalkyl, nitro, halogen and $C_1$-$C_4$-alkyl, $R_4$ and $R_5$ independently of one another are hydrogen, halogen, $C_1$-$C_4$-halogenoalkyl, $C_1$-$C_4$-alkyl, $C_2$-$C_4$-alkenyl, $C_3$-$C_6$ cycloalkyl, methoxy or nitro and X is oxygen or sulfur, it being also possible for X—$R_3$, together with $R_4$ or $R_5$ in the ortho position, to be the group —O—$CF_2$—O—$CF_2$—, and (B) one or more synthetic pyrethroid(s).

For example, compositions according to the invention contain compounds of the formula (1) in which $R_1$ and $R_2$ independently of one another are $C_1$-$C_4$-alkyl or $C_2$-$C_4$-alkenyl, $R_3$ is $C_1$-$C_4$-halogenoalkyl or phenyl which is substituted by $C_1$-$C_4$-halogenoalkyl, $R_4$ and $R_5$ independently of one another are hydrogen, halogen, $C_1$-$C_4$-halogenoalkyl, methoxy or nitro and, in the event that X—$R_3$ is 4-trifluoromethylphenoxy, $R_4$ and $R_5$ are additionally $C_1$-$C_4$-alkyl, $C_2$-$C_4$-alkenyl or cyclopropyl in the 2-position and/or the 6-position, and X is oxygen or sulfur, it being also possible for X—$R_3$, together with $R_4$ or $R_5$ in the ortho-position, to be the group —O—$CF_2$—O—$CF_2$—.

the 5-phenylcarbamoylbarbiturates of the formula (1) (component (A)) exist in various tautomeric forms (keto/enol tautomerism), for instance in accordance with the following diagram:

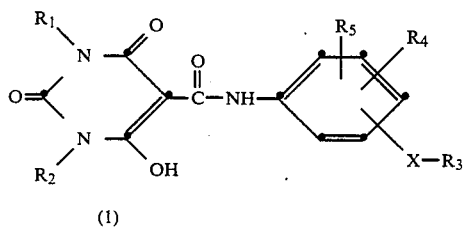

(1)

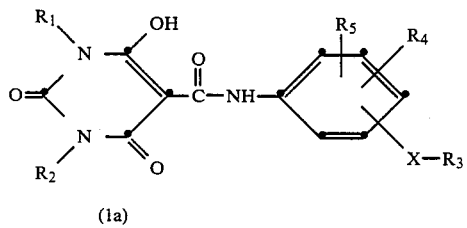

(1a)

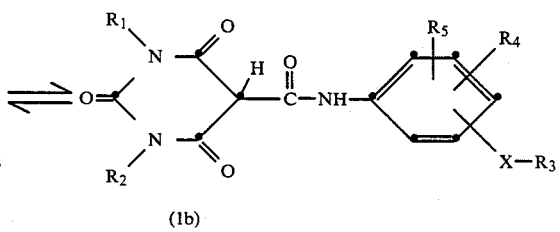

(1b)

All the tautomeric forms and mixtures thereof can be employed in the composition according to the invention. The individual formulae also include, therefore, the tautomeric forms possible in a particular case.

The active compounds of the formula (1) can also be employed in the form of their salts in the composition according to the invention. The alkali metal, ammonium or amine salts should be mentioned particularly, and sodium, potassium, ammonium or alkylamine, especially triethylamine, salts are preferred.

It is preferable to employ 5-phenylcarbamoylbarbituric acid compounds of the formula (1) in which X is oxygen.

In preferred compounds of the formula (1), the substituent —X—$R_3$ is in the ortho-position or the para-position. In formula (1), $R_1$ and $R_2$ are preferably $C_1$-$C_4$-alkyl, especially methyl or ethyl.

The substituents $R_4$ and/or $R_5$ are preferably hydrogen, $C_1$-$C_4$-alkyl or halogen, especially chlorine.

"Halogen" is to be understood as meaning particularly fluorine, chlorine or bromine, chlorine and fluorine being preferred.

Preferred $C_1$-$C_4$-halogenoalkyl radicals (substituents $R_3$, $R_4$ and $R_5$ in formula (1)) are those containing 1 or 2 C atoms and 1 to 5 identical or different halogen atoms, in particular fluorine or chlorine atoms. The following are examples of these: 1,1,2-trifluoro-2-chloroethyl, 1,1,2,2-tetrafluoroethyl, 1,1,2,2-tetrafluoro-2-chloroethyl, chlorodifluoromethyl, dichlorofluoromethyl, dichloromethyl, difluoromethyl, trichloromethyl and, in particular, trifluoromethyl.

In further preferred compounds of the formula (1), $R_3$ is a $C_1$-$C_4$-halogenoalkyl radical, especially one of those listed above as examples, and X is oxygen.

Other compositions according to the invention which have a particularly good action are those which contain, as the component A, a compound of the formula (1) in which X is oxygen and $R_3$ is a phenyl radical which is substituted by 1 to 3, preferably 1 to 2, substituents belonging to the group comprising $C_1$-$C_4$-halogenoalkyl, halogen or $C_1$-$C_4$-alkyl, the radical —X—$R_3$ being preferably in the ortho-position or the para-position. In this connection, preferred agents are also those in which, in the component (A) of the formula (1), $R_4$ and $R_5$ are in the 2-position and/or the 6-position and are hydrogen or $C_1$-$C_4$-alkyl and —X—$R_3$ is 4-trifluoromethylphenoxy.

The second component (component B) of the active compound combination according to the invention is a synthetic pyrethroid. Pyrethroids which are preferred in compositions according to the invention belong to the class comprising cyclopropanecarboxylic acid esters or α-alkyl (especially isopropyl)-phenylacetic acid esters, i.e. they contain the structural elements

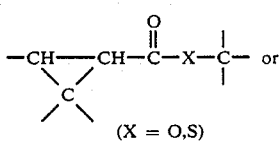 or

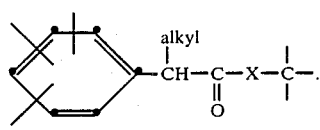

Examples of the pyrethroid component employed are compounds of the general formula

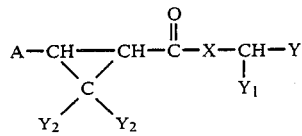 (2)

in which A is

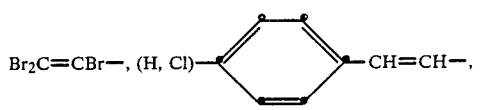

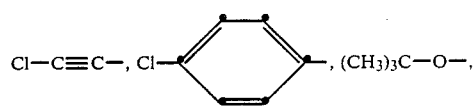

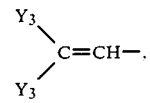

in which $Y_3$ is Cl, Br, $CF_3$, F or $C_1$-$C_4$-alkyl, or A is $CH_2$=CH—$CH_2$—O— or

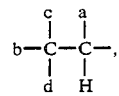

in which a, b, c and d independently of one another are Cl, Br or F, and c and d can also be methyl, X is oxygen or sulfur, $Y_1$ is hydrogen, CN, $CH_3$, $C_2H_5$, i—$C_3H_7$,

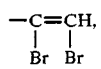

—C≡CH, —C≡C—$CH_3$, —C≡C—$C_6H_5$, —CH=CH—$CH_3$, —$CH_2$—CH=$CH_2$, —CH=$CH_2$ or —CH$_2$—CH=CHCL, $Y_2$ is methyl or the two $Y_2$s together are the portion required to complete a cyclopropane, cyclobutane or cyclopentane ring and Y is

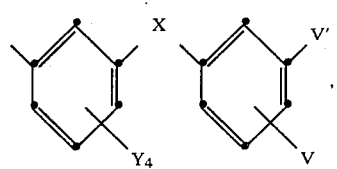

in which $Y_4$ is hydrogen or fluorine and V is hydrogen, Cl, Br, F, $CH_3$ or $NO_2$ and V' is hydrogen, it being also possible for V' to be $CF_3$ in the event that V is hydrogen, and X is as defined above; and Y is also

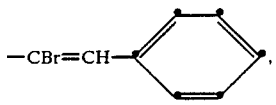

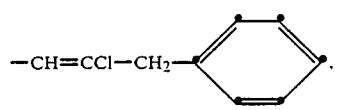

-continued

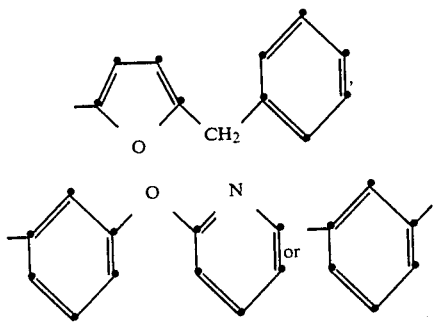

which $V_1$ is $-CH_2-CH=CH_2$, $-CH_2-C\equiv CH$, $-CH_2-CH=CH-CH_3$,

$-CF=CFCl$ or $-CF=CF_2$; or of the general formula

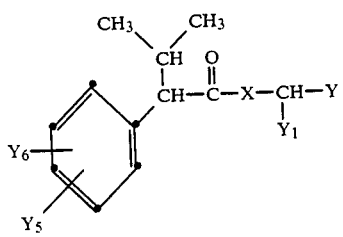

in which X, Y and $Y_1$ are as defined in formula (2), $Y_5$ is hydrogen, $CH_3$, Cl, $NO_2$, $OCH_3$, $OCH(CH_3)_2$, $-OCH_2C\equiv CH$ or $-OCH_2CH=CH_2$ and $Y_6$ is hydrogen, $CH_3$, Cl, Br or F, or $Y_5$ and $Y_6$ in the ortho-position together are the portion required to complete a fused benzene ring, the compounds of the formula (2) being used preferentially.

Components (B) which can be employed particularly preferentially are those of the formula (2) defined above in which A is a radical of the formula

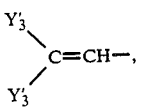

in which $Y_3'$ is Br, Cl or $CH_3$, X is oxygen and Y is

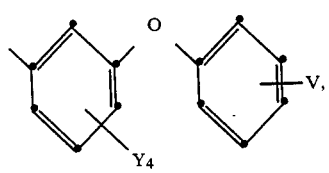

In formula (2), $Y_2$ is preferably $CH_3$ and $Y_1$ is preferably hydrogen, CN, $CH_3$, $-CH=CH_2$, $-C\equiv CH$ or $-C\equiv C-CH_3$, especially hydrogen or CN.

In compositions according to the invention which are of practical importance, the component (B) is a compound belonging to the class comprising 3''-phenoxybenzyl 3-(2',2'-dihalogenovinyl)-2,2-dimethylcyclopropanecarboxylates, in particular a compound of the formula

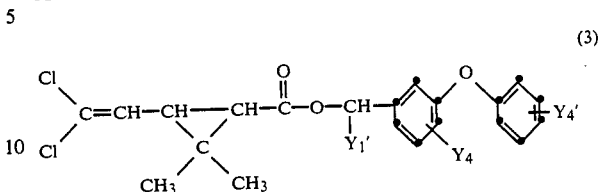

in which $Y_1'$ is hydrogen, cyano, $-CH=CH_2$ or $-C\equiv C-CH_3$ and $Y_4$ and $Y_4'$ independently of one another are hydrogen or fluorine. The common name of the compound of the formula (3) in which $Y_1'=Y_4=Y_4'=$hydrogen is Permethrin, while that in which $Y_1'=CN$ and $Y_4=Y_4{}^{40}=$hydrogen is Cypermethrin.

The compositions according to the invention can consist exclusively of the components (A) and (B) or they can also contain, additionally, customary carriers or formulating agents, such as solvents, water, acids, bases, surfactants, wetting agents, dispersing agents and/or emulsifiers.

Examples of suitable solvents are organic solvents, for example aliphatic and alicyclic alcohols, ketones, hydrocarbons, such as benzene, xylenes, toluene or petroleum ether fractions, and also chlorinated and fluorinated hydrocarbons and, in particular, propylene glycol, methoxyethanol, ethoxyethanol or dimethylformamide, if appropriate as a mixture with water.

Examples of further suitable formulating agents are the customary surface-active substances which are used as wetting agents, dispersing agents and/or emulsifiers, for example those which are mentioned later in the text as additives for application baths in the process according to the invention.

It is particularly advantageous for the compositions according to the invention to contain formulation ingredients which produce a formulation which is stable on storage and can be used without further treatment. Formulation ingredients of this type are described in European Patent Specification No. 74,355 (in that text see components C to G). The present invention also relates, therefore, to compositions containing the components (A) and (B) and also the components C to G described in the said European patent text. These components which are described in that text and their preferred representatives and also the relative ratios thereof are declared to form a part of the present description.

The pyrethroids of the formula (2) (component (B)) are known. In this connection, see, for example, the literature references on page 1. Some of the 5-phenylcarbamoylbarbiturates of the formula (1) are known from European Patent Specification No. 7,541 or they can be obtained by the processes quoted in that text. The preparation of some compounds of the formula (1) which are not mentioned in that text is described in the preparation instructions in the experimental section below.

The ratio in which the two active compound components (A) and (B) are mixed in the compositions according to the invention (active compound combinations) can vary within wide limits; for example, it can be between 1:4 and 4:1, preferably between 1:2 and 2:1. In agents according to the invention which are particularly preferred, this ratio is about 1:1.

The compositions according to the invention can be employed to protect keratin material against keratin-consuming insects, for example against keratin-consuming larvae of Lepidoptera, for example Tineola spec. and Tinea spec. and also against keratin-consuming larvae of Coleoptera, for example Anthrenus spec. and Attagenus spec. The compositions are excellently suitable for protecting keratin material or keratin-containing material against being eaten by insects, especially for imparting a finish which is fast to washing and light and resistant to insects, especially for imparting a finish to materials of this type which is resistant to moths and beetles. It is possible to impart a finish to keratin material or keratin-containing material both in a crude state and in a processed state, for example raw or processed sheeps' wool, products composed of other animal hairs, skins, furs and feathers.

A factor of particular importance in practice is the effectiveness of the agents according to the invention against the larvae of the common clothes moth (*Tineola bisselliella*), the case-making clothes moth (*Tinea pellionella*) and the brown house moth (*Hofmannophila pseudopretella*) and against the larvae of the fur beetle and the carpet beetle (Attagenus spec. and Anthrenus spec., respectively), for example the variegated blossom beetle (*Anthrenus verbasci*), the pimpernel blossom beetle (*Anthrenus pimpinellae*), the common carpet beetle (*Anthrenus scrophilariae*), the banded carpet beetle (*Anthrenus fasciatus*), the common fur beetle (*Attagenus pellio*) and, particularly, the black carpet beetle (*Attagenus piceus*) and the furniture carpet beetle (*Anthrenus vorax*).

The compositions according to the invention are preferably employed, firstly, for protecting woolen textiles, for example woolen blankets, woolen carpets, woolen laundry goods, woolen garments and knitted goods or textile materials made of or containing wool, such as mixed fabrics in which one component is wool, for example mixed fabrics made of wool and other natural fibres, preferably cotton, or of wool and synthetic fibres, and, secondly, also for protecting furs and skins against attack by the pests mentioned.

The present invention also relates to a process for protecting keratin material, in particular woolen textiles, against attack by keratin pests, for example moth and beetle larvae, which comprises treating the material to be protected with a combination of one or more 5-phenylcarbamoylbarbiturate(s) of the formula (1) and one or more synthetic pyrethroid(s), preferably those of the formulae (2) and (2a). This is effected, as a rule, by introducing this active compound combination, which can, as a composition according to the invention, also contain, if appropriate, customary carriers or formulation auxiliaries, into an application liquor, to which it is also possible to add, if appropriate, customary textile auxiliaries and/or dyes, and using this liquor to impregnate the material to be protected. The two active compound components (A) and (B) can, of course, be added separately to the application liquor.

The materials to be protected, in particular textile materials, can, for example, be impregnated by means of hot or cold aqueous dyebaths, bleaching baths, chroming baths or after-treatment baths containing a specific fraction of an active compound combination according to the invention, various textile finishing processes, for example the padding or exhaustion process, being suitable.

The treatment is advantageously carried out at temperatures from 10° to 100° C., preferably at about 60°–100° C. in a dyebath or preferably at 10 to 70, in particular 20° to 60° C., in an after-treatment bath or washing bath.

Examples of additional auxiliaries which can be added to the application liquors are dispersing agents, emulsifiers or surfactants, insofar as sufficient of these has not already been introduced by means of the composition according to the invention. In addition, the liquor can also contain customary auxiliaries, such as water-soluble perborates, polyphosphates, carbonates, silicates, fluorescent brightening agents, softeners, salts having an acid reaction, such as ammonium silicofluoride or zinc silicofluoride, or certain organic acids, such as oxalic acid, acetic acid or particularly formic acid, and also antimicrobial agents and finishing agents, for example those based on synthetic resins, or starch. If the moth-resistant and beetle-resistant finishing process is carried out together with the dyeing of the material (for example wool), the liquors also contain, additionally, the corresponding dyes and, if necessary, the auxiliaries required for the purpose, for example levelling agents.

Aqueous application liquors can contain, for example, surfactants, for example anionic compounds, such as soaps and other carboxylates (for example alkali metal salts of higher fatty acids), derivatives of sulfur-oxygen acids (for example the sodium salt of dodecylbenzenesulfonic acid, water-soluble salts of the sulfuric acid monoesters of higher-molecular alcohols or polyglycol ethers thereof, such as, for instance, soluble salts of sulfated dodecyl alcohol or of sulfated dodecyl alcohol polyglycol ether), derivatives of phosphorus-oxygen acids (for example phosphates), derivatives containing acid (electrophilic) nitrogen in the hydrophilic group (for example disulfinic salts), cationic surfactants, such as amines and salts thereof (for example lauryldiethylenetriamine), onium compounds or amine oxides, or nonionic surfactants, such as polyhydroxy compounds, surfactants based on monosaccharides or polysaccharides, higher-molecular acetylene glycols or polyglycol ethers (for example polyglycol ethers of higher fatty alcohols or polyglycol ethers of phenols containing higher-molecular alkyl substituents).

If non-aqueous application (solvent application) is carried out, an appropriate part of a composition according to the invention (active compound combination) can also be added to a suitable solvent and the material to be protected can be impregnated with the solution thus obtained. Solvents which are suitable for this purpose are, inter alia, trichloroethylene, methylene chloride, hydrocarbons, propylene glycol, methoxyethanol, ethoxyethanol and dimethylformamide, and it is also possible to add thereto dispersing agents (for example emulsifiers, such as sulfated castor oil, fatty alcohol sulfates and the like) and/or other auxiliaries. The materials to be protected are usually simply impregnated with these solutions.

It is also possible, however, to combine the finishing of the materials to be protected with a dry cleaning process. An appropriate part of a composition according to the invention (active compound combination) is dissolved, for this purpose, in the cleaning agent (for instance lower halogenated alkanes, for example trichloroethylene and the like), and the cleaning process is carried out in a customary manner.

It is also possible, however, to dissolve a proportion of a composition according to the invention (active compound combination) in readily volatile organic solvents and then to spray this solution onto the substrate to be protected (spray application). Textiles made of or containing wool, and furs and feathers, are especially suitable for this mode of application. The advantage of spray application consists in the fact that pollution of the effluent is avoided because the solvents are recovered.

In the process according to the invention, the compositions according to the invention can also be used in combination with other protective agents which are effective against keratin-consuming insects, for example in combination with urea derivatives, benzimidazoles, aromatic sulfonamides and phosphoric and phosphonic acid esters.

The quantity of composition according to the invention (active compound combination according to the invention) employed, which is introduced into the particular application bath or non-aqueous solvent depends on the particular substrate and the method of application. This quantity is usually such that, after absorption to the particular material to be protected, the latter contains about 10 to 2,000 ppm, preferably 100 to 1,000 ppm, of the combination of active substances, i.e. of barbiturate+pyrethroid (of component(A)+(B)), the upper limit being largely set by considerations of a economic nature, while the lower limit depends on criteria such as the breadth and permanence of protective action desired. For example, for the exhaustion process at a liquor ratio of 1:20, this results in concetrations of 0.001 to 1 g of active substance per liter of treatment bath, depending on the degree of exhaustion achievable. In the padding process concentrations of up to 2 g of active substance per liter are possible.

In the following preparation instructions and examples, unless otherwise specified, parts are parts by weight and percentages are percentages by weight. The designations "Permethrin" and "Cypermethrin" are to be understood as meaning the compounds of the formula (3) defined above in which $Y_1'=Y_4=Y_4'=$hydrogen and in which $Y_1'=CN=CN$ and $Y_4=Y_4'=$hydrogen, respectively.

Preparation instructions for some 5-phenylcarbamoylbarbituric acids of the formula (1):

1. 13.7 g (0.06 mol) of 1,3-dimethyl-5-ethoxycarbonylbarbituric acid and 16.9 g (0.06 mol) of 2,6-dimethyl-4-(4-trifluoromethylphenoxy)-aniline are thoroughly mixed with one another and heated under an atmosphere of protective gas (nitrogen) for 1 hour at 160° C. (external temperature), in the course of which ethanol is evolved. The reaction is completed by heating the contents of the flask at 180° C. (external temperature) for a further 10 minutes, then cooling to room temperature and recrystallising twice from 1:1 toluene/hexane. This gives 19.6 g of 1,3-dimethyl-5-[2,6-dimethyl-4-(4-trifluoromethylphenoxy)]-carbamoylbarbituric acid of the formula

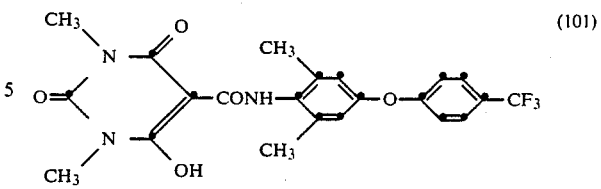

with a melting point of 189°–191° C.

2. 9.1 g (0.04 mol) of 1,3-dimethyl-5-ethoxycarbonylbarbituric acid and 11.8 g (0.4 mol) of 2-isopropyl-4-(4-trifluoromethylphenoxy)-anikine are thoroughly mixed with one another and heated under an atmosphere of protective gas (nitrogen) for 1 hour at 160° C. (external temperature), ethanol being evolved. The reaction is completed by heating the contents of the flask at 180° C. (external temperature) for a further 10 minutes, then cooling to room temperature and recrystallising twice from petroleum ether. This gives 11.8 g of 1,3-dimethyl-5-[2-isopropyl-4-(4-trifluoromethylphenoxy)]-carbamoylbarbituric acid of the formula

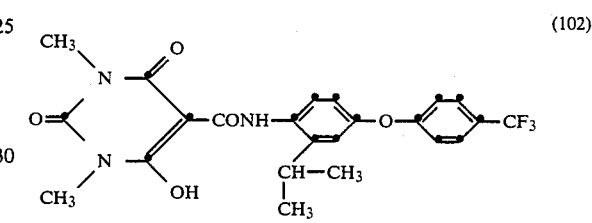

with a melting point of 158°–159° C.

The remaining 5-phenylcarbamoylbarbituric acids embraced by the formula (1) can be obtained analogously to the above procedure. Alternatively, the compounds of the formula (1) can also be obtained by the process described in European Patent Specification No. 7,541, namely by reacting a barbituric acid of the formula

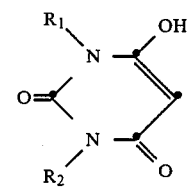

with an isocyanate of the formula

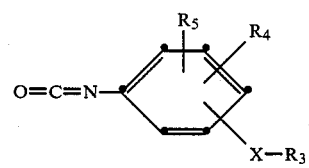

under the conditions indicated in the said European patent. Some of the compounds embraced by the formula (1) are known from European Patent Specification No. 7,541.

EXAMPLE 1

A 0.4% stock solution in ethylene glycol monomethyl ether of a 1:1 mixture of the compound of the formula (101) and Permethrin is prepared. Aqueous application liquors containing, in 120 ml of distilled water, 0.12 ml of a wetting and dispersing agent, 0.6 ml of 1:10 formic acid and 0.2 ml, 0.1 ml or 0.05 ml of th 0.4% stock solution are then prepared at room temperature. Pieces of woolen flannel fabric, each weighing 3 g, are then thoroughly wetted with hot water and are introduced at room temperature. The bath temperature is increased to 98° C. in the course of 20 minutes, with continuous agitation of the woolen sample, and is kept at 98° C. for 60 minutes. The bath is then cooled and the woolen sample is rinsed twice with distilled water for 3 minutes, squeezed out by hand and dried in the air. The concentration of active compound is 250, 125 or 60 ppm, calculated on the weight of wool.

The sample dried in this way is subjected to the test for moth resistance (protection against being eaten by the common clothes moth *Tineol abisselliella* Hum.) prescribed by the instructions of the Swiss Standard Association SNV 195,901 and to the test for resistance to the larvae of the fur beetle (*Attagenus piceus* Ol.) and the furniture carpet beetle (*Anthrenus vorax* Wat.) as prescribed in SNV 195,902.

In each case larvae of *Anthrenus vorax* and 6 to 7 week old larvae of *Attagenus piceus* are used for the test. Pieces of the same size are cut out from the treated woolen flannel samples and are exposed to the attack (eating) of groups of 15 larvae of the appropriate pest for 14 days at a constant temperature (28° C.) and a constant relative humidity (65%). Assessment is made firstly on the basis of the relative loss in weight of the test specimen and secondly on the basis of the number of organisms still alive.

The mixture of active compounds tested shows an excellent action against all 3 pests used and at all the concentrations employed.

The procedure described above is repeated, except that a 1:1 mixture of the compound of the formula (101) and Cypermethrin or the pyrethroid of the formula

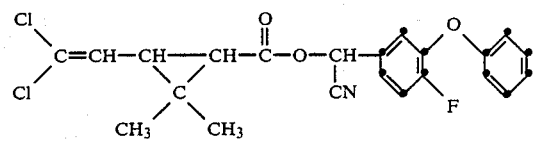

(201)

or a 1:1 mixture of the compound of the formula (102) and Permethrin, Cypermethrin or the compound of the formula (201) is used, affording similarly a fabric to which a completely moth-resistant and beetle-resistant finish has been imparted.

EXAMPLE 2

One or more of the following compounds can also be employed as the pyrethroid component (component (B)) in the finishing process according to Example 1: 3-phenoxy-α-vinylbenzyl and 3-phenoxy-α-methylethinylbenzyl 3-(2,2-dichlorovinyl)-2,2-dimethylcyclopropanecarboxylates, 4-fluoro-3-phenoxybenzyl and 4-fluoro-3-phenoxy-α-cyanobenzyl 3-(2-methylpropen(1)yl)-2,2-dimethylcyclopropanecarboxylates, 4-fluoro-3-phenoxybenzyl and 4-fluoro-3-phenoxy-α-ethinylbenzyl 3-(2,2-dichlorovinyl)-2,2-dimethylcyclopropanecarboxylates, 4-fluoro-3-phenoxybenzyl, 4-fluoro-3-phenoxy-α-cyanobenzyl and 4-fluoro-3-phenoxy-α-ethinylbenzyl 3-(2,2-dibromovinyl)-2,2-dimethylcyclopropanecarboxylates, 4-fluoro-3-(4-fluorophenoxy)-α-cyanobenzyl 3-(2-methylpropen(1)-2,2-dimethylcyclopropanecarboxylate, 4-fluoro-3-(3-fluorophenoxy)-benzyl, 4-fluoro-3-(3-fluorophenoxy)-α-cyanobenzyl, 4-fluoro-3-(4-fluorophenoxy)-benzyl and 4-fluoro-3-(4-fluorophenoxy)-α-cyanobenzyl 3-(2,2-dichlorovinyl)-2,2-dimethylcyclopropanecarboxylates, 4-fluoro-3-(3-fluorophenoxy)-benzyl, 4-fluoro-3-(3-fluorophenoxy)-α-cyanobenzyl and 4-fluoro-3-(4-fluorophenoxy)-α-cyanobenzyl 3-(2,2-dibromovinyl)-2,2-dimethylcyclopropanecarboxylates, 4-fluoro-3-phenoxy-α-cyanobenzyl 3-(2-chloro-2-(4-chlorophenyl)-vinyl)-2,2-dimethylcyclopropanecarboxylate, 2-[or 3-]-fluoro-3-[or 4-]fluorophenoxy)-α-cyanobenzyl 3-(2,2-dichlorovinyl)-2,2-dimethylcyclopropanecarboxylate,

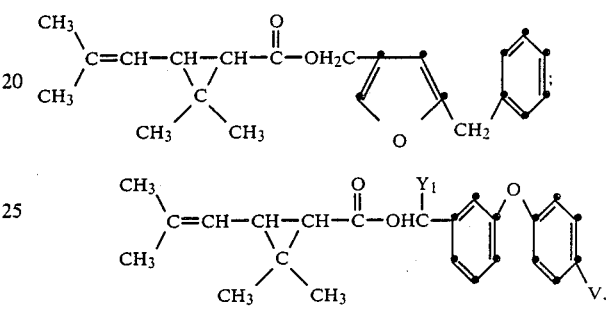

in which V=H, Cl, Br, F, CH₃ or NO₂ and Y₁=H, CN, Ch₃, C₂H₅, i—C₃H₇, $$-\underset{Br}{C}=\underset{Br}{CH},$$

—C≡CH, C≡C—CH₃, —CH=CH₂, —CH=CH—CH₃, —CH₂—CH=CH₂ or —CH₂—CH=CHCl;

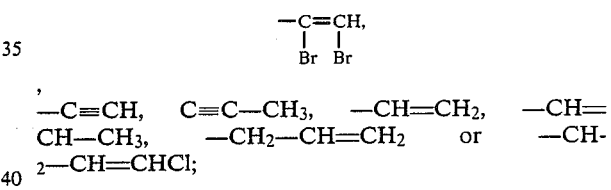

in which Y₁—H, CN or CH₃;

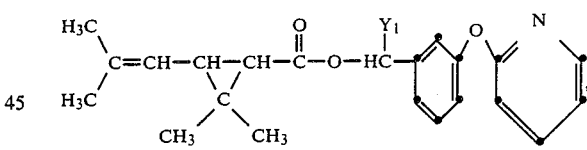

in which Y₁=H, CN or —C≡CH;

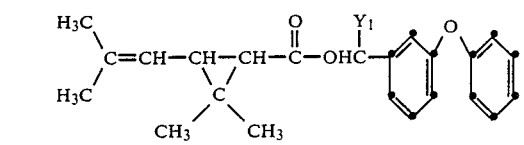

in which
V=H, Cl, Br, F, CH₃ or NO₂ and
Y₁=H, CN, CH₃, C₂H₅, i—C₃H₇,

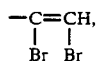
, —C≡CH, —C≡C—CH₃, —CH=CH₂, —CH=CH—CH₃, —CH₂—CH=CH₂, —CH₂—CH=CHCl or —C≡C—C₆H₅;

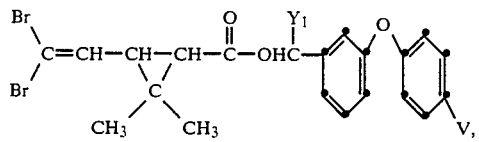

in which
V=H, Cl, Br, F, CH₃ or NO₂ and
$Y_1$=H, CN, CH₃, C₂H₅, i—C₃H₇,

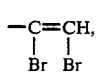

—C≡CH, —C≡C—CH₃, —CH=CH₂, —CH=CH—CH₃, —CH₂—CH=CH₂, —CH₂—CH=CHCl or —C≡C—C₆H₅;

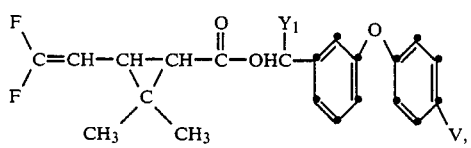

in which
V=H, Cl, Br, F, CH₃ or NO₂ and $Y_1$=H, CN, CH₃, C₂H₅, i—C₃H₇,

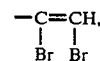

—C≡CH, —C≡C—CH₃, —CH=CH₂, —CH=CH—CH₃, —CH₂—CH=CH₂, —CH₂—CH=CHCl or —C≡C—C₆H₅;

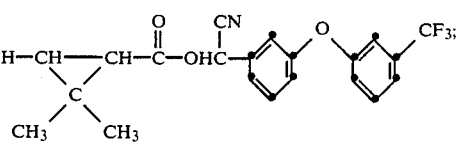

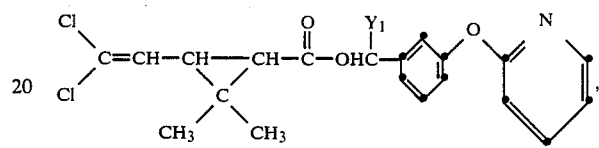

in which $Y_1$=H, CN or CH₃;

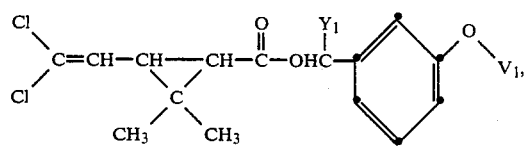

in which
$Y_1$=H, CN, or CH₃ and
$V_1$=CH₂—CH=CH₂, —CH₂—C≡CH, —CH₂—CH=CH—CH₃,

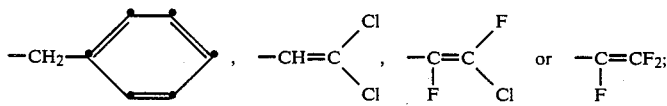

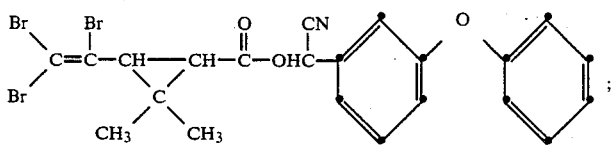

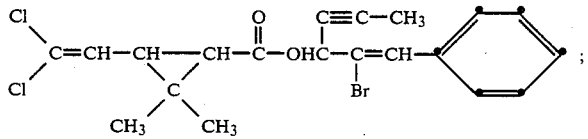

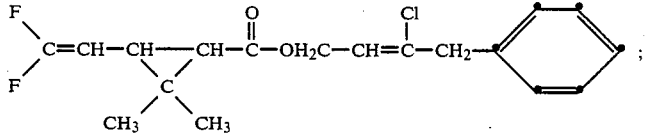

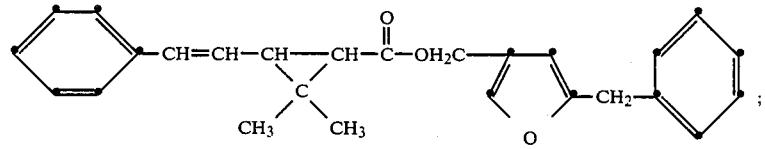

-continued

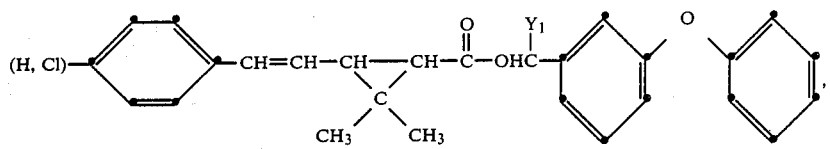

in which $Y_1$=H, CN, $CH_3$, $C_2H_5$, i—$C_3H_7$, $$-\underset{\underset{Br}{|}}{\overset{\overset{Br}{|}}{C}}=CH,$$

—C≡CH, —C≡C—$CH_3$, —CH=$CH_2$, —CH=CH—$CH_3$, —$CH_2$—CH=$CH_2$ or —$CH_2$—CH=CHCl;

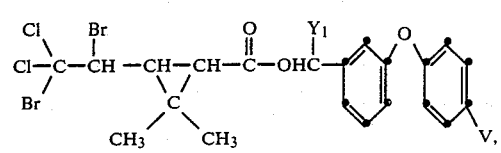

in which
V=H, Cl, Br, F, $CH_3$ or $NO_2$ and
$Y_1$=H, CN, $CH_3$, $C_2H_5$, i—$C_3H_7$, $$-\underset{\underset{Br}{|}}{\overset{\overset{Br}{|}}{C}}=CH,$$

—C≡CH, —C≡C—$CH_3$, —CH=$CH_2$, —CH=CH—$CH_3$, —$CH_2$—CH=$CH_2$ or —$CH_2$—CH=CHCl;

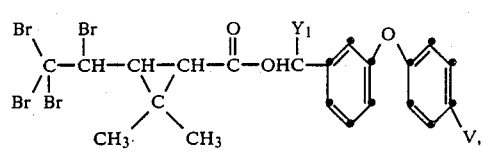

in which
V=H, Cl, Br, F, $CH_3$ or $NO_2$ and
$Y_1$=H, CN, $CH_3$, $C_2H_5$, i—$C_3H_7$, $$-\underset{\underset{Br}{|}}{\overset{\overset{Br}{|}}{C}}=CH,$$

—C≡CH, —C≡C—$CH_3$, —CH=CH—$CH_3$, —$CH_2$—CH=$CH_2$ or —$CH_2$—CH=CHCl;

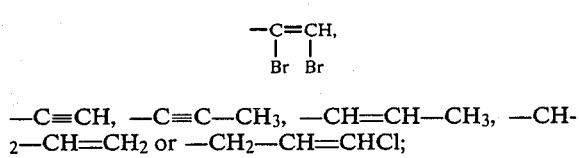

in which
V=H, Cl, Br, F, $CH_3$ or $NO_2$ and
$Y_1$=H, CN, $CH_3$, $C_2H_5$, i—$C_3H_7$, $$-\underset{\underset{Br}{|}}{\overset{\overset{Br}{|}}{C}}=CH,$$

—C≡CH, —C≡C—$CH_3$, —CH=$CH_2$, —CH=CH—$CH_3$, —$CH_2$—CH=$CH_2$ or —$CH_2$—CH=CHCl;

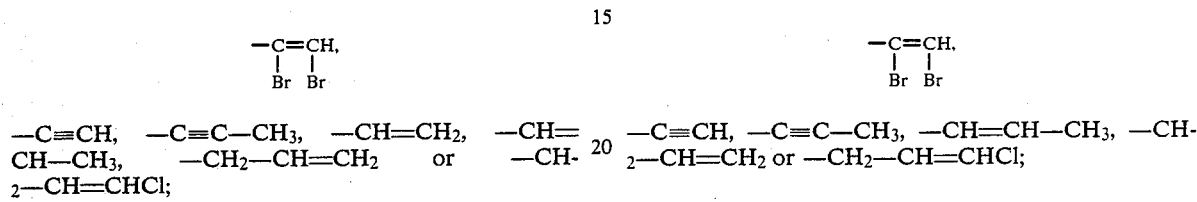

in which
V=H, Cl, Br, F, $CH_3$ or $NO_2$ and
$Y_1$=H, CN, $CH_3$, $C_2H_5$, i—$C_3H_7$, $$-\underset{\underset{Br}{|}}{\overset{\overset{Br}{|}}{C}}=CH,$$

—C≡CH, —C≡C—$CH_3$, —CH=CH—$CH_3$, —$CH_2$—CH=$CH_2$ or —$CH_2$—CH=CHCl;

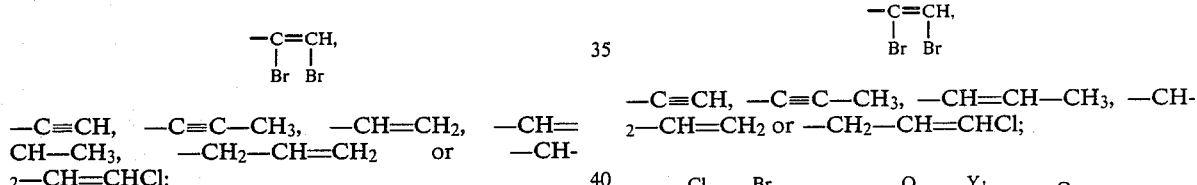

in which
$Y_1$=H or CN;

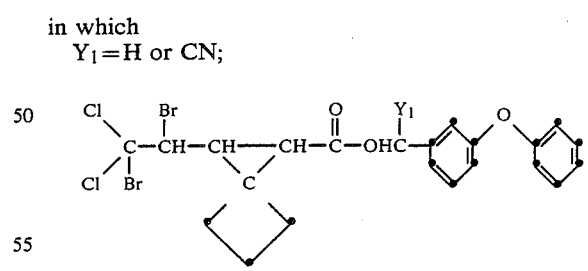

in which $Y_1$=H or CN;

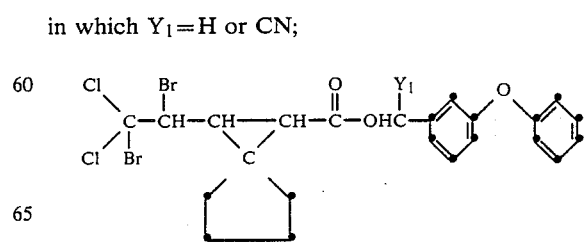

in which $Y_1$=H or CN;

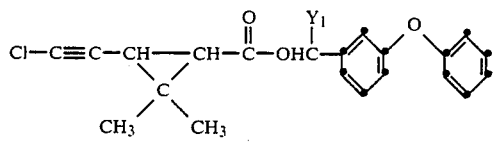

in which $Y_1$=H, CN or —CH=CH—CH$_3$;

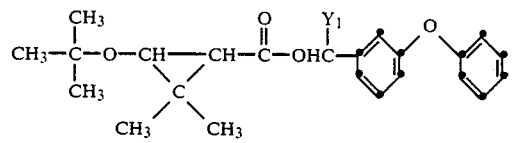

in which $Y_1$=H or CN;

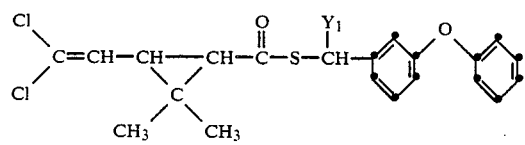

in which $Y_1$=H, CN$_3$ or CN;

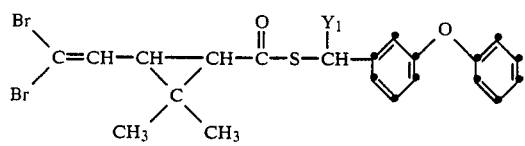

in which $Y_1$=H or CH$_3$;

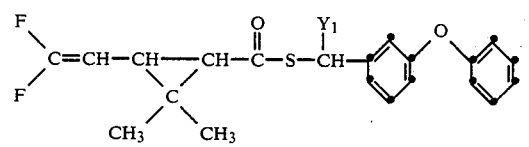

in which X=H or CH$_3$;

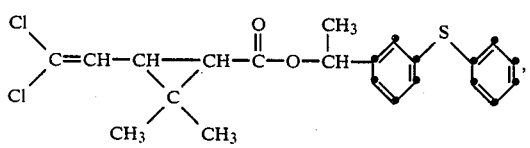

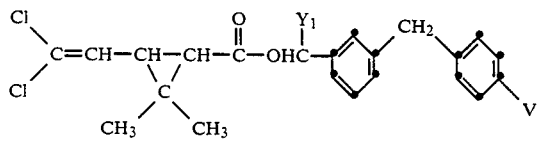

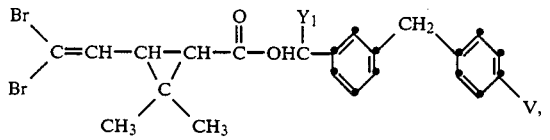

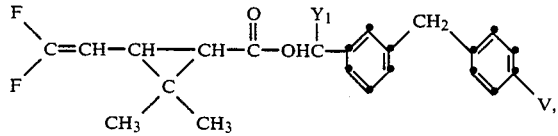

-continued

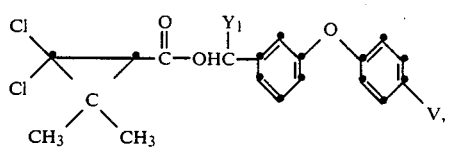

in which in each case
V =H, Cl, Br, F, CH$_3$ or NO$_2$ and
$Y_1$=H, CN, CH$_3$, C$_2$H$_5$, i—C$_3$H$_7$,

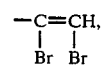

—C≡CH, —C≡C—CH$_3$, —CH=CH$_2$, —CH=CH—CH$_3$, —CH$_2$—CH=CH$_2$, —CH$_2$—CH=CHCl or —C≡C—C$_6$H$_5$;

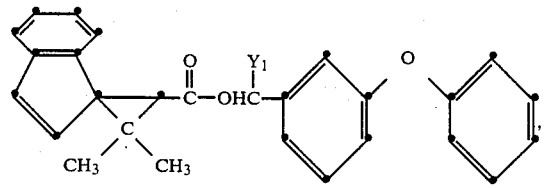

in which $Y_1$=H, CN, CH$_3$ or —C≡C—CH$_3$;

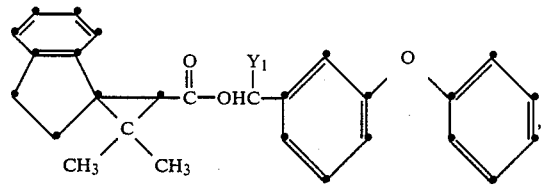

in which $Y_1$=H, CN, CH$_3$ or —C≡C—CH$_3$;

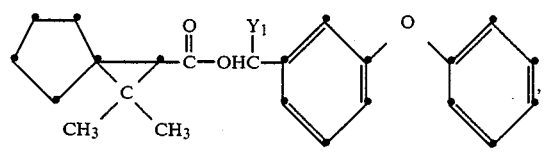

in which $Y_1$=H, CN, CH$_3$ or —C≡C—CH$_3$;

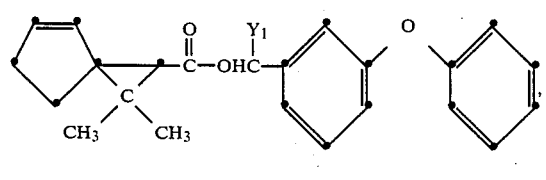

in which $Y_1$=H, CN, CH$_3$ or —C≡C—CH$_3$;

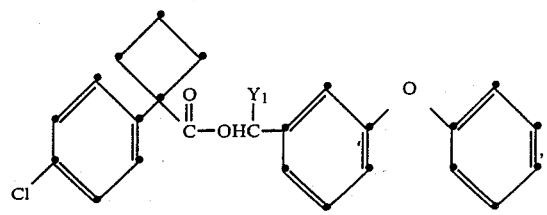

in which $Y_1 = H$, CN or —C≡CH;

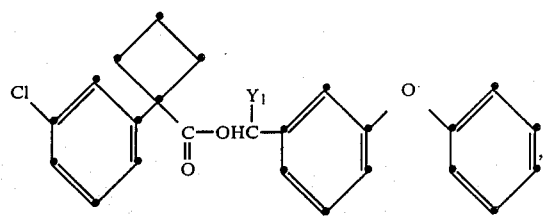

in which $Y_1 = H$ or CN;

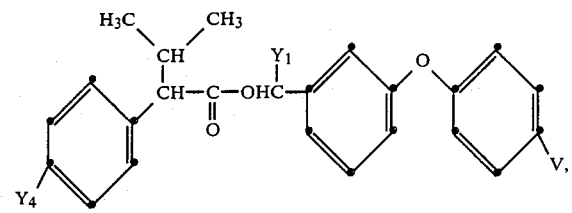

in which
$V = H$, Cl, Br, F, $CH_3$ or $NO_2$ and $Y_1 = H$, CN, $CH_3$, $C_2H_5$, i—$C_3H_7$,

—C≡CH, —C≡C—$CH_3$, —CH=$CH_2$, —CH=CH—$CH_3$, —$CH_2$—CH=$CH_2$, —$CH_2$—CH=CHCl or —C≡C—$C_6H_5$ and
$Y_4 = H$, $CH_3$Cl, $NO_2$, CN, —$OCH_3$,

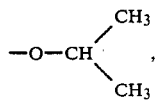

—O—$CH_2$—C≡CH or —O—$CH_2$—CH=$CH_2$;

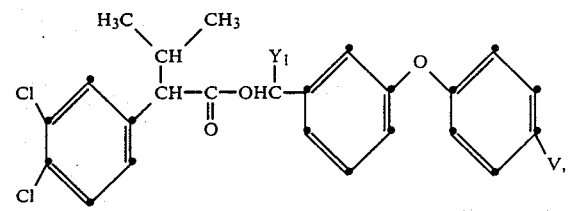

in which
$V = H$, Cl, Br, F, $CH_3$ or $NO_2$ and
$Y_1 = H$, CN, $CH_3$, $C_2H_5$, i—$C_3H_7$,

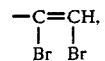

—C≡CH, —C≡C—$CH_3$, —CH=$CH_2$, —CH=CH—$CH_3$, —$CH_2$—CH=$CH_2$ or —$CH_2$—CH=CHCl;

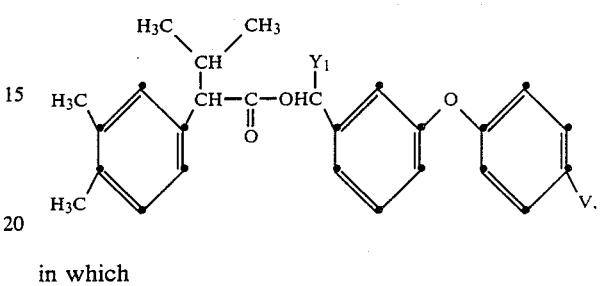

in which
$V = H$, Cl, Br, F, $CH_3$ or $NO_2$ and
$Y_1 = H$, CN, $CH_3$, $C_2H_5$, i—$C_3H_7$,

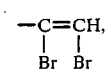

—C≡CH, —C≡C—$CH_3$, —CH=$CH_2$, —CH=CH—$CH_3$, —$CH_2$—CH=$CH_2$ or —$CH_2$—CH=CHCl;

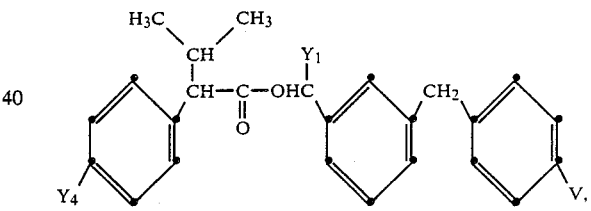

in which
$V = H$, Cl, Br, F, $CH_3$ or $NO_2$ and
$Y_1 = H$, CN, $CH_3$, $C_2H_5$, i—$C_3H_7$,

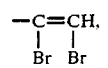

—C≡CH, —C≡C—$CH_3$, —CH=$CH_2$, —CH=CH—$CH_3$, —$CH_2$—CH=$CH_2$ or —$CH_2$—CH=CHCl
and
$Y_4 = H$, $CH_3$, Cl, $NO_2$, CN, —$OCH_3$,

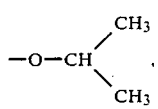

—$OCH_2$—C≡CH or —O—$CH_2$—CH=$CH_2$;

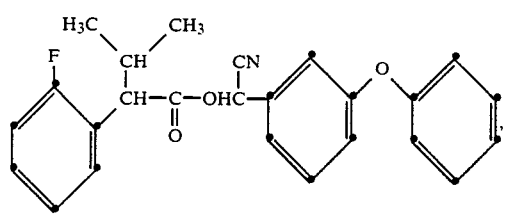
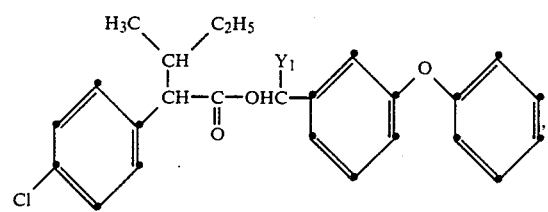
in which $Y_1$=H or CN;
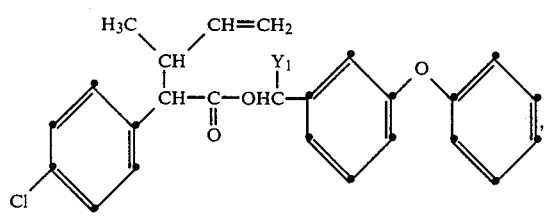
in which $Y_1$=H or CN;
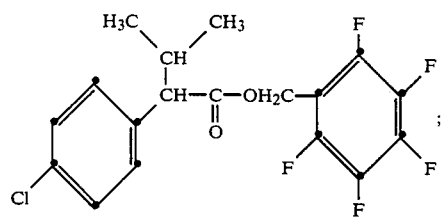
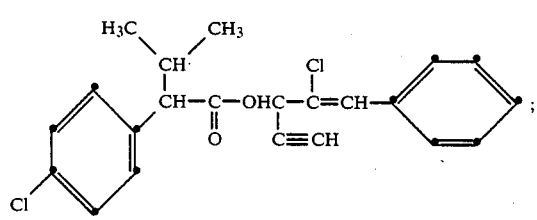
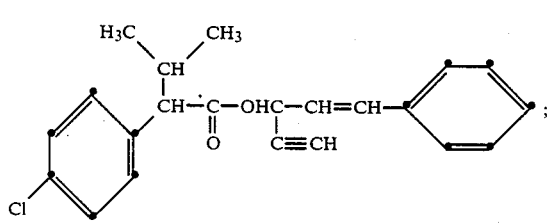
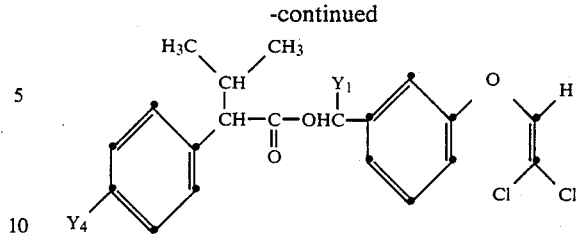
in which
$Y_1$=H, CN or $CH_3$ and
$Y_4$=H or Cl;
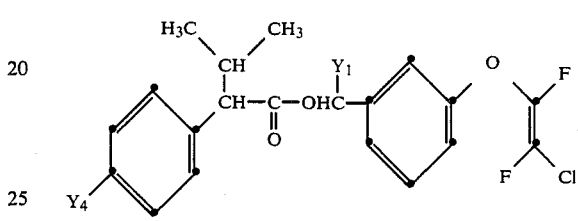
in which
$Y_1$=H, CN or $CH_3$ and
$Y_4$=H or Cl;
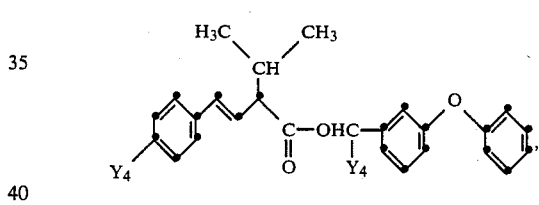
in which
$Y_1$=H, CN or $CH_3$ and
$Y_4$=H or $CH_3$;
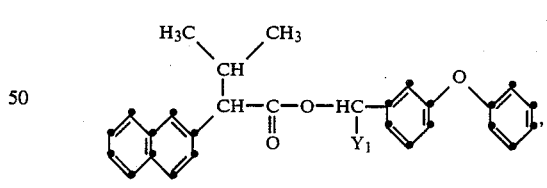
in which $Y_1$=H or CN;
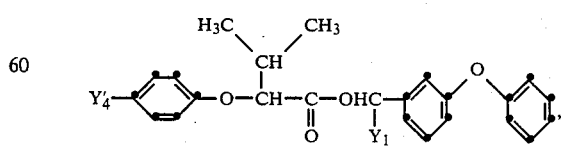
in which
$Y_1$=H or CN and
$Y_4'$=Cl, $CH_3$ or H;

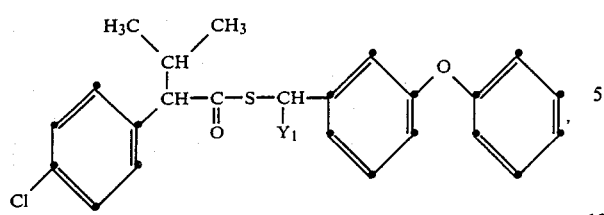

in which $Y_1$=H, $CH_3$, —C≡CH or CN;

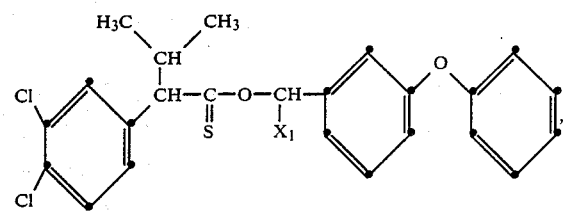

in which $Y_1$=H or CN;

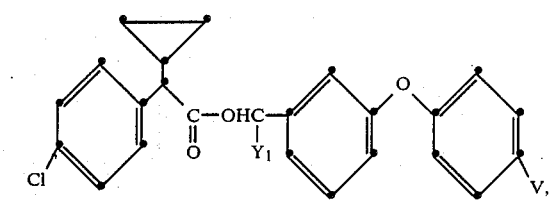

in which
V=H, Cl, Br, F, $CH_3$ or $NO_2$ and
$Y_1$=H, CN, $CH_3$, $C_2H_5$, i—$C_3H_7$,

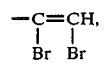

—C≡CH, —C≡C—$CH_3$, —CH=$CH_2$, —CH=CH—$CH_3$, —$CH_2$—CH=$CH_2$ or —$CH_2$—CH=CHCl.

EXAMPLE 3

In the finishing process according to Example 1 or 2, it is also possible to employ, as the barbiturate component (component (A)), one or more of the compounds of the general formula

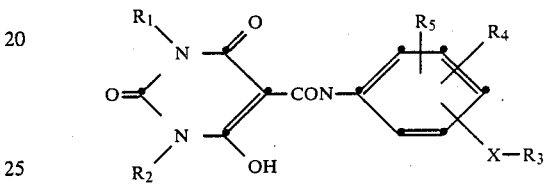

Listed in Table 1 below, instead of those already mentioned in Example 1.

TABLE 1

| Compound No. | $R_1$ | $R_2$ | $R_4$ | $R_5$ | $X$—$R_3$ | Melting point (°C.) |
|---|---|---|---|---|---|---|
| 103 | cyclohexyl (H) | $CH_3$ | 2-CH($CH_3$)$_2$ | H | 4-O—C$_6$H$_4$—$CF_3$ | 157–158 |
| 104 | $CH_3$ | $CH_3$ | 2-$CH_2$ | H | 4-O—C$_6$H$_4$—$CF_3$ | 163–165 |
| 105 | $CH_3$ | $CH_3$ | H | H | 4-O—C$_6$H$_4$—$CF_3$ | 192–194 |
| 106 | cyclopropyl | $CH_3$ | 2-$CH_3$ | 6-$CH_3$ | 4-O—C$_6$H$_4$—$CF_3$ | 147–149 |
| 107 | cyclohexyl (H) | $CH_3$ | 2-$CH_3$ | 6-$CH_3$ | 4-O—C$_6$H$_4$—$CF_3$ | 100–102 |
| 108 | $CH_2$CH=$CH_2$ | $CH_3$ | 2-$CH_3$ | 6-$CH_3$ | 4-O—C$_6$H$_4$—$CF_3$ | 139–140 |
| 109 | $CH_3$ | $CH_3$ | 3-Cl | H | 4-$OCF_3$ | 160 |
| 110 | $C_2H_5$ | $C_2H_5$ | 3-Cl | H | 4-$OCF_3$ | 134–135 |
| 111 | $C_2H_5$ | $CH_3$ | 2-Cl | H | 4-$OCF_3$ | 119 |
| 112 | $C_2H_5$ | $CH_3$ | 3-Cl | H | 4-$OCF_2$CHClF | 124 |
| 113 | $C_2H_5$ | $CH_3$ | H | H | 4-$OCF_2CF_2$H | 119 |
| 114 | $C_2H_5$ | $CH_3$ | H | H | 4-$OCF_3$ | 118–120 |
| 115 | $C_2H_5$ | $CH_3$ | 3-Cl | H | 4-$OCF_3$ | 130–132 |
| 116 | $C_2H_5$ | $CH_3$ | H | H | 3-$OCF_2$CHClF | 98–99 |
| 117 | $C_2H_5$ | $CH_3$ | 3-Cl | H | 4-$SCF_2$Cl | 138–140 |
| 118 | $C_2H_5$ | $CH_3$ | H | H | 4-$SCF_3$ | 142 |
| 119 | $C_2H_5$ | $CH_3$ | H | H | 3,4-O—$CF_2$—O—$CF_2$— | 98–100 |

TABLE 1-continued

| Compound No. | R₁ | R₂ | R₄ | R₅ | X—R₃ | Melting point (°C.) |
|---|---|---|---|---|---|---|
| 120 | C₂H₅ | CH₃ | H | H | 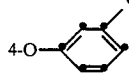 | 172–180 |
| 121 | C₂H₅ | CH₃ | 3-CF₃ | H | 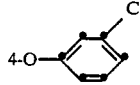 | 63–70 |
| 122 | C₂H₅ | CH₃ | 3-Cl | H | 4-O—CF₃ | |
| 123 | C₂H₅ | CH₃ | 3-Cl | H | 4-S—CF₃ | |
| 124 | CH₃ | CH₃ | 3-Cl | H | 4-SCF₃ | |
| 125 | C₂H₅ | C₂H₅ | 3-Cl | H | 4-SCF₃ | |
| 126 | C₂H₅ | CH₃ | 2-Cl | H | 4-OCF₃ | |
| 127 | CH₃ | CH₃ | 2-Cl | H | 4-OCF₃ | |
| 128 | C₂H₅ | C₂H₅ | 3-Cl | H | 4-OCF₂CHClF | |
| 129 | CH₃ | CH₃ | 3-Cl | H | 4-OCF₂CHClF | |
| 130 | CH₃ | CH₃ | H | H | 4-OCF₃ | |
| 131 | CH₃ | CH₃ | H | H | 4-OCF₂CHF₂ | |
| 132 | CH₃ | C₂H₅ | H | H | 4-OCF₂CHF₂ | |
| 133 | CH₃ | CH₃ | H | H | 3-OCF₂CHClF | |
| 134 | CH₃ | C₂H₅ | 3-Cl | H | 4-OCF₂CF₂Cl | |
| 135 | CH₃ | CH₃ | 3-Cl | H | 4-SCF₂Cl | |
| 136 | CH₃ | C₂H₅ | H | H | 3-SCF₃ | |
| 137 | CH₃ | CH₃ | 2-CH(CH₃)₂ | H | 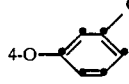 | 143–145 |
| 138 | CH₃ | CH₃ | H | H | 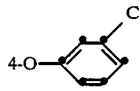 | 197–199 |
| 139 | CH₃ | CH₃ | H | H | 2,3-O—CF₂—O—CF₂— | |
| 140 | CH₃ | CH₃ | 5-Cl | H | 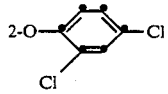 | 240–241 |
| 141 | CH₃ | CH₃ | H | H | 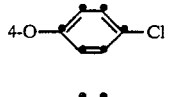 | 209–210 |
| 142 | CH₃ | CH₃ | 4-Cl | H | 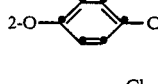 | 255–256 |
| 143 | CH₃ | CH₃ | 2-CH₃ | 6-CH₃ | 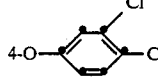 | 210–212 |
| 144 | CH₃ | CH₃ | 3-Cl | H | 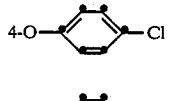 | 183–184 |
| 145 |  | CH₃ | 3-Cl | H | 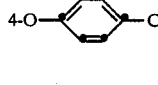 | 141–142 |
| 146 | CH₃ | CH₃ | 3-Cl | 4-Cl | 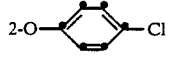 | 270–272 |
| 147 | CH₃ | CH₃ | H | H | 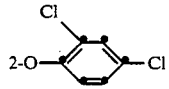 | 215–217 |

TABLE 1-continued

| Compound No. | R₁ | R₂ | R₄ | R₅ | X—R₃ | Melting point (°C.) |
|---|---|---|---|---|---|---|
| 148 | CH₃ | CH₃ | H | H |  2-O—⟨⟩—CH₃ | 240–243 |
| 149 | CH₃ | CH₃ | 4-Cl | H |  2-O—⟨⟩—F | 220–223 |
| 150 | CH(CH₃)₂ | CH₃ | 4-Cl | H |  2-O—⟨⟩—Cl | 170–173 |
| 151 | CH₃ | CH₃ | H | H |  Cl / 2-O—⟨⟩—Cl | 198–200 |
| 152 | CH₃ | CH₃ | 3-Cl | 4-Cl |  2-O—⟨⟩ | 132–138 |
| 153 | CH₃ | CH₃ | 3-Cl | 4-Cl | 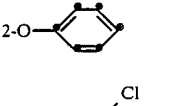 Cl / 2-O—⟨⟩ | 120–122 |
| 154 | CH₃ | CH₃ | 4-CH₃ | H |  Cl / 2-O—⟨⟩—Cl | 221–223 |
| 155 | CH₃ | CH₃ | 3-Cl | H | 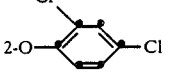 2-O—⟨⟩—F | >250 |
| 156 | CH₃ | CH₃ | 4-Cl | H |  Cl / 2-O—⟨⟩—Cl | 238–240 |
| 165 | —CH₂—CH=CH₂ | —CH₂—CH=CH₂ | 4-Cl | H |  2-O—⟨⟩—Cl | 182–185 |
| 166 | CH₃ | CH₃ | 4-Cl | H | 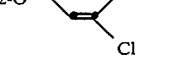 2-O—⟨⟩—Cl, Cl, Cl | 268–270 |
| 167 | CH₃ | CH₃ | 2-C₂H₅ | 6-CH(CH₃)(C₂H₅) | 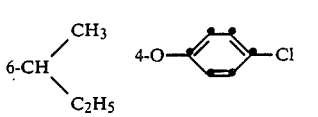 4-O—⟨⟩—Cl | 124–126 |
| 168 | CH₃ | CH₃ | H | H | 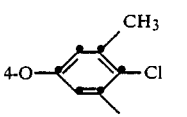 CH₃ / 4-O—⟨⟩—Cl / CH₃ | 234–235 |
| 169 | CH₃ | CH₃ | 2-CH₃ | 6-CH₃ |  Cl / 4-O—⟨⟩—CF₃ | 172–173 |
| 170 | CH₃ | CH₃ | 2-OCH₃ | H | 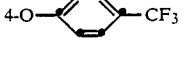 Cl / 3-O—⟨⟩—CF₃ | 188–189 |

TABLE 1-continued

| Compound No. | $R_1$ | $R_2$ | $R_4$ | $R_5$ | $X-R_3$ | Melting point (°C.) |
| --- | --- | --- | --- | --- | --- | --- |
| 171 | cyclopropyl | $CH_3$ | H | H | 2-O—(2,5-dichlorophenyl), Cl | 202–203 |

EXAMPLE 4

A 0.4% stock solution in ethylene glycol monomethyl ether of a 1:1 mixture of the compound of the formula (101) and Permethrin is prepared. 12.5 ml of the appropriate stock solution are diluted to 50 ml (solution No. 2) with ethylene glycol monomethyl ether containing 0.65 g/liter of a wetting and dispersing agent. 25 ml of solution No. 2 are again diluted to 50 ml (solution No. 3) with ethylene glycol monomethyl ether containing 0.5 g/liter of a wetting and dispersing agent.

3 ml of each of solutions Nos. 1, 2 and 3 are poured into crystallisation dishes and in each case a baited circle of woolen flannel is wetted in the appropriate dish for 3 seconds. The moist circles are then padded between aluminum foil in such a way that, after being squeezed out, each of the circles has picked up 50% of liquor. The concentration of active compound on the circles is then 500 ppm, 250 ppm and 125 ppm respectively.

The moist circles are dried in the air and subjected to the same biological tests as those described in Example 1.

The active compound mixture tested shows an excellent action against all 3 pests and at all the concentrations used.

The procedure described above is repeated, except that a 1:1 mixture of the compound of the formula (101) and Cypermethrin or the compound of the formula (201), or another combination of active compounds indicated in Example 1, or an active compound combination, according to the invention, taken from Examples 2 and 3, is used, affording similarly a fabric to which a completely moth-resistant and beetle-resistant finish has been imparted.

EXAMPLE 5

A 10% solution in ethylene glycol monomethyl ether of a 1:1 mixture of the compound of the formula (101) and Permethrin is prepared. One part by volume of this solution is diluted with 200 parts by volume of a solvent suitable for dry cleaning, for example an appropriate petroleum ether fraction or perchloroethylene. If desired, cleansing-promoting additives can also be added. Woolen articles are then treated in a customary manner in this cleaning fluid and are then centrifuged to a solvent content of approx. 100% of the weight of wool. After drying they show a protective action against the keratin-consuming pests mentioned above.

EXAMPLE 6

0.5% solutions in methylene chloride, trichloroethylene or a low-boiling petroleum ether fraction, of a 1:1 mixture of the compound of the formula (102) and Permethrin are made up. A woolen article is then sprayed with one of these solutions by means of a conventional spray device, so that $2 \times 15$ g/m² of active compound solution are applied. If the utilisation of the aerosol is 30%, there are then about 400 ppm of the active compound combination on the material. The woolen fabric finished in this manner shows a good protective action against the keratin-consuming pests mentioned above.

The procedure described in Examples 5 and 6 is repeated, except that a 1:1 mixture of the compound of the formula (101) and Cypermethrin or the compound of the formula (201), or another active compound combination indicated in Example 1 or an active compound combination, according to the invention, taken from Examples 2 and 3, is used, affording similarly a fabric which is protected against attack by keratin pests.

If they are not added direct, as such, to application baths, the active compound combinations according to the invention can also be formulated by adding various carriers, solvents and/or auxiliaries. Particularly advantageous formulations, which are stable on storage, are obtained if the two active compound components according to the invention are formulated in the manner indicated in European Patent Specification No. 74,335, i.e. a formulation is prepared which, in addition to the two components (A) and (B), also contains one or more aliphatic or cycloaliphatic amine(s) and/or amide(s) and derivative(s) thereof and, if appropriate, one or more organic solvent(s), water, one or more surfactant(s) and/or emulsifier(s) or dispersing agent(s) and/or one or more aliphatic carboxylic acid(s). The active compound combinations according to the invention can, therefore, be formulated as described in Examples 1–25 of the said European Patent Specification No. 74,335. The two formulations following are intended to serve as examples:

EXAMPLE 7

5.3 parts of Permethrin, 8.0 parts of 1-hydroxyethyl-2-oleylimidazoline, 7.0 parts of tallow fatty amine ethoxylated with 6–7 mol of ethylene oxide, 73.7 parts of diethylene glycol ethyl ether and 1.0 part of racemic lactic acid are mixed. 5.0 parts of the compound of the formula (102) are added to this mixture at 45°–55° C., with continuous stirring, until a homogeneous formulation is formed. The mothproofing formulation thus obtained is stable on storage, miscible with water and, when applied to keratin material, produces excellent moth-resistant and beetle-resistant finishes.

EXAMPLE 8

A formulation of the following composition is obtained analogously to Example 7: 5.5 parts of Permethrin, 5.0 parts of the compound of the formula (101), 20.0 parts of tallow fatty amine ethoxylated with 6–7 mol of ethylene oxide, 5.0 parts of a block polymer formed from propylene glycol and ethylene oxide (average molecular weight: 4,900, 80% of hydrophobic groups, 20% of hydrophilic groups; HLB=4), 7.0 parts of castor oil polyglycol ether, 3.0 parts of a partial alkyl ester of phosphoric acid and 54.5 parts of isophorone (=3,5,5-trimethyl-2-cyclohexen-1-one).

EXAMPLE 9

A formulation of the following composition is obtained analogously to Example 7: 5.5 parts of Permethrin, 5.0 parts of the compound of the formula (101), 45.0 parts of the compound of the formula

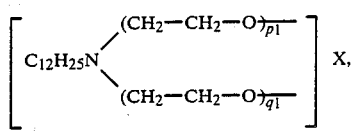

in which $P_1+q_1=8$ and X is an acid phosphoric acid radical, 20.0 parts of a block polymer formed from propylene glycol and ethylene oxide (average molecular weight: 6,350; 50% of hydrophobic and 50% of hydrophilic groups; HLB=15), 12.5 parts of the Na salt of sulfated nonylphenol ethoxylated with 40 mol of ethylene oxide, 7.0 parts of ethylpolyglycol and 5.0 parts of polyethylene glycol 300.

Replacing Permethrin by Cypermethrin or the compound of the formula (201), or replacing Permethrin and a compound of the formula (101) or (102) by another active compound combination indicated in Example 1 or by an active compound combination, according to the invention, taken from Examples 2 and 3, in the formulations of Examples 7-9 also gives advantageous formulations which are stable on storage and can be used for imparting a finish to keratin material against attack by keratin pests.

EXAMPLE 10

Dyeing and simultaneously imparting a moth-resistant and beetle-resistant finish:

A piece of woolen fabric is wetted out in a dyeing machine for 5 minutes at 40° C. (liquor ratio 1:20) in 600 g of a dye liquor consisting of 1.5 g of the formulation according to Example 7, 8 or 9, 30.3 g of sodium sulfate decahydrate, 24.0 g of concentrated sulfuric acid, 3.0 g of a red dye of the formula

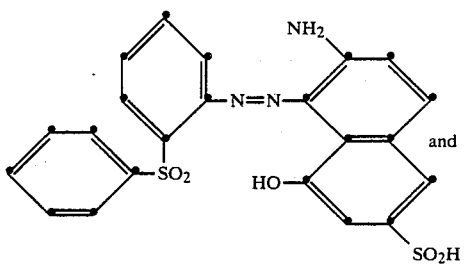

541.5 g of deionised water. The liquor is then heated to approx. 98° C. in the course of 45 minutes. After a treatment of 1 hour at this temperature, the woolen fabric is rinsed and dried. The dye and the two active compounds present in the particular formulation are absorbed into the fabric. After this single-bath treatment, the red-colored woolen fabric is completely protected against being eaten by moth and beetle larvae. This is established by testing resistance as prescribed in SNV Standards 195,901 and 195,902.

EXAMPLE 11

Use in an after-treatment bath:

A piece of woolen fabric is wetted out in a dyeing machine for 5 minutes at 30° C. (liquor ratio 1:20) in 400 g of an after-treatment liquor consisting of 1 g of the formulation according to Example 7, 8 or 9, 4 g of 85% formic acid and 395 g of deionised water. The liquor is then heated to 45° C. in the course of 20 minutes. After being treated for 30 minutes at this temperature, and being kept under continuous agitation, the woolen fabric is thoroughly rinsed in cold water and dried. The woolen fabric treated in this way is completely protected against the larvae of wool pests.

What is claimed is:

1. A composition for protecting keratin material against attack by keratin pests, which contains (A) one or more 5-phenylcarbamoylbarbiturate(s) of the formula

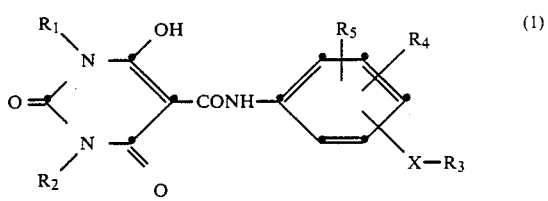

or tautomeric forms or salts thereof, in which $R_1$ and $R_2$ independently of one another are $C_1$-$C_4$-alkyl, $C_3$-$C_6$-cycloalkyl, $C_2$-$C_4$-alkenyl, benzyl, phenyl or phenyl which is substituted by 1 to 3 substituents belonging to the group comprising halogen, $C_1$-$C_4$-alkyl, $C_1$-$C_4$-alkoxy and nitro, $R_3$ is $C_1$-$C_4$-halogenoalkyl, phenyl or phenyl which is substituted by 1-3 substituents belonging to the group comprising $C_1$-$C_4$-halogenoalkyl, nitro, halogen and $C_1$-$C_4$-alkyl, $R_4$ and $R_5$ independently of one another are hydrogen, halogen, $C_1$-$C_4$-halogenoalkyl, $C_1$-$C_4$-alkyl, $C_2$-$C_4$-alkenyl, $C_3$-$C_6$ cycloalkyl, methoxy or nitro and X is oxygen or sulfur, it being also possible for X—$R_3$, together with $R_4$ or $R_5$ in the ortho-position, to be the group —O—$CF_2$—O—$CF_2$—, and (B) one or more synthetic pyrethroid(s).

2. A composition of claim 1, which contains, as the component (A), a compound of the formula in which $R_1$ and $R_2$ independently of one another are $C_1$-$C_4$-alkyl or $C_2$-$C_4$-alkenyl, $R_3$ is $C_1$-$C_4$-halogenoalkyl or phenyl which is substituted by $C_1$-$C_4$-halogenoalkyl, $R_4$ and $R_5$ independently of one another are hydrogen, halogen, $C_1$-$C_4$-halogenoalkyl, methoxy or nitro and, in the event that X—$R_3$ is 4-trifluoromethylphenoxy, $R_4$ and $R_5$ are additionally $C_1$-$C_4$-alkyl, $C_2$-$C_4$-alkenyl or cyclopropyl in the 2-position and/or the 6-position, and X is oxygen or sulfur, it being also possible for X—$R_3$, together with $R_4$ or $R_5$ in the ortho-position, to be the group —O—$CF_2$—O—$CF_2$—.

3. A composition of claim 1, which contains, as component (A), a compound of the formula in which X is oxygen, $R_1$ and $R_2$ are $C_1$-$C_4$-alkyl, and the substituent —X—$R_3$ is in the ortho-position or the para-position.

4. A composition of claim 1, which contains, as component (A), a compound of the formula in which $R_4$ and $R_5$ are in the 2-position and/or the 6-position and are hydrogen or $C_1$-$C_4$-alkyl and —X—$R_3$ is 4-trifluoromethylphenoxy.

5. A composition of claim 1, which contains, as the component, a compound of the formula in which X is oxygen and $R_3$ is $C_1$-$C_4$-halogenoalkyl.

6. A composition of claim 1, which contains, as the component, a compound of the formula in which X is oxygen and $R_3$ is a phenyl radical which is substituted by 1 to 3 substituents belonging to the group comprising $C_1$-$C_4$-halogenoalkyl, halogen or $C_1$-$C_4$-alkyl.

7. A composition of claim 1, which contains, as component (B), a synthetic pyrethroid belonging to the class comprising cyclopropanecarboxylic acid esters or α-alkylphenylacetic acid esters.

8. A composition according to claim 7, which contains, as the component (B), a pyrethroid of the formula

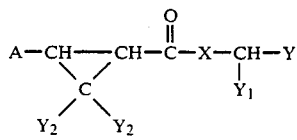

in which A is

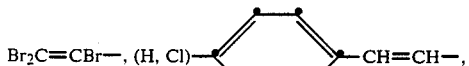

in which $Y_3$ is Cl, Br, $CF_3$, F or $C_1$-$C_4$-alkyl, or A is $CH_2$=CH—$CH_2$—O— or

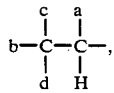

in which a, b, c and d independently of one another are Cl, Br or F, and c and d can also be methyl, X is oxygen or sulfur, $Y_1$ is hydrogen, CN, $CH_3$, $C_2H_5$, i—$C_3H_7$,

—C≡CH, —C≡C—$CH_3$, —C≡C—$C_6H_5$, —CH=CH—$CH_3$, —$CH_2$—CH=$CH_2$, —CH=$CH_2$ or —$CH_2$—CH=CHCl, $Y_2$ is methyl or the two $Y_2$s together are the portion required to complete a cyclopropane, cyclobutane or cyclopentane ring and Y is

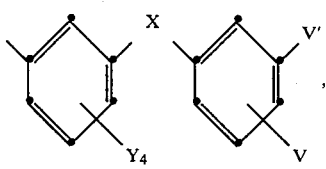

in which $Y_4$ is hydrogen or fluorine and V is hydrogen, Cl, Br, F, $CH_3$ or $NO_2$ and V' is hydrogen, it being also possible for V' to be $CF_3$ in the event that V is hydrogen, and X is as defined above; and Y is also

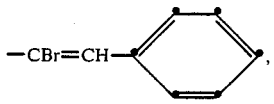

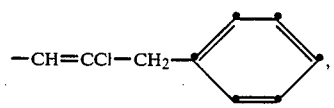

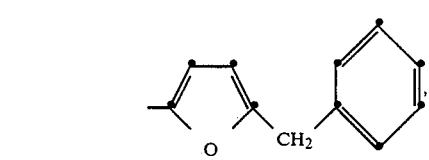

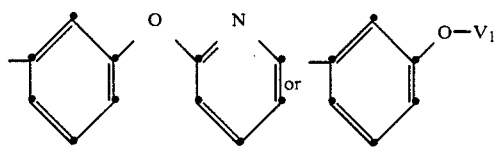

in which $V_1$ is —$CH_2$—CH=$CH_2$, —$CH_2$—C≡CH, —$CH_2$—CH=CH—$CH_3$,

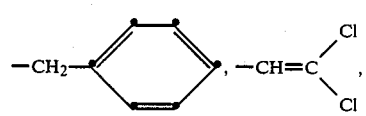

—CF=CFCl or —CF=$CF_2$; or of the formula

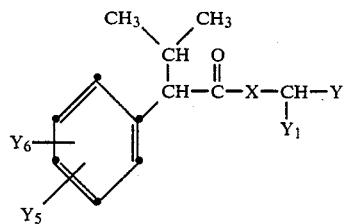

in which X, Y and $Y_1$ are as defined above, $Y_5$ is hydrogen, $CH_3$, Cl, $NO_2$, $OCH_3$, $OCH(CH_3)_2$, —$OCH_2$C≡CH or —$OCH_2$CH=$CH_2$ and $Y_6$ is hydrogen, $CH_3$, Cl, Br or F, or $Y_5$ and $Y_6$ in the ortho-position together are the portion required to complete a fused benzene ring.

9. A composition of claim 8, which contains, as component (B), a pyrethroid of the first formula in which A is a radical of the formula

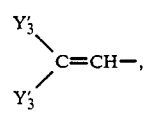

in which $Y_3'$ is Br, Cl or $CH_3$, X is oxygen and Y is

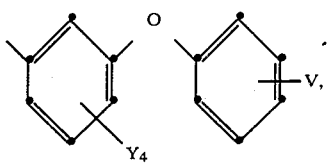

and $Y_2$ is $CH_3$ and $Y_1$ is hydrogen, CN, $CH_3$, $-CH=CH_2$, $-C\equiv CH$ or $-C\equiv C-CH_3$.

10. A composition of claim 1, which in addition to the components (A) and (B), also contains at least one of the following: a carrier, an organic solvent, water, an acid, a base, a wetting agent, a dispersing agent and an emulsifier.

11. A composition of claim 10, which, in addition to the components (A) and (B) contains an aliphatic or cycloaliphatic amine or amide or derivative thereof.

12. A composition of claim 11 which further contains at least one of the following ingredients: an organic solvent, water, a surfactant, an emulsifier a dispersing agent and an aliphatic carboxylic acid.

13. A process for protecting or finishing keratinous material, in particular wool, furs, feathers and skins, from attack by keratin pests, which comprises the step of treating the material to be protected with an effective amount of a combination consisting essentially of a 5-phenylcarbamoylbarbiturate (A) of the formula

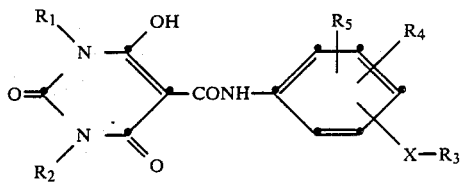

or a tautomeric form or a salt thereof, in which $R_1$ and $R_2$ independently of one another are $C_1-C_4$-alkyl, $C_4-C_6$-cycloalkyl, $C_2-C_4$-alkenyl, benzyl, phenyl or phenyl which is substituted by 1 to 3 substitutents belonging to the group comprising halogen, $C_1-C_4$-alkyl, $C_1-C_4$-alkoxy and nitro, $R_3$ is $C_1-C_4$-halogenoalkyl, phenyl or phenyl which is substituted by 1–3 substituents belonging to the group comprising $C_1-C_4$-halogenoalkyl, nitro, halogen and $C_1-C_4$-alkyl, $R_4$ and $R_5$ independently of one another are hydrogen, halogen, $C_1-C_4$-halogenoalkyl, $C_1-C_4$-alkyl, $C_2-C_4$-alkenyl, $C_3-C_6$ cycloalkyl, methoxy or nitro and X is oxygen or sulfur, it being also possible for $X-R_3$, together with $R_4$ and $R_5$ in the ortho-position, to be the group $-O-CF_2-O-CF_2-$, and (B) a synthetic pyrethroid.

14. A process of claim 13 wherein in component (A), X is oxygen, R, and $R_2$ are $C_1-C_4$-alkyl and the substituent $-X-R_3$ is in the ortho-position or the para-position, and wherein in component (B) A is a radical of the formula

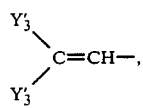

in which $Y_3'$ is Br, Cl or $CH_3$, X is oxygen and Y is

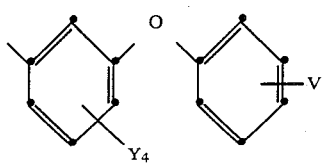

and $Y_2$ is $CH_3$ and $Y_1$ is hydrogen, CN, $CH_3$, $-CH=CH_2$, $-C\equiv CH$ or $-C\equiv C-CH_3$.

15. A process of claim 13, employing a composition which, in addition to the combination of active compounds, also contains at least one of the following customary carriers and formulation auxiliaries: an organic solvent, water, an acid, a base, a wetting agent, a dispersing agent and an emulsifier.

16. A process of claim 13, wherein the material to be protected is treated with an aqueous liquor containing an active compound combination defined in claim 12, using the exhaustion process or the padding process.

17. A process of claim 13, wherein the material to be protected is treated with an organic cleaning fluid containing an active compound combination defined in claim 12.

18. A process of claim 13, wherein the material to be protected is sprayed with an organic solvent containing an active compound combination defined in claim 12.

19. A process of claim 13, wherein the active compound combination is applied to the materials to be protected in an amount of 10 to 2,000 ppm based on the material to be protected.

20. The keratin material to which a finish according to claim 13 has been imparted.

21. A keratinous material according to claim 20, preferably textiles made of or containing wool, furs or skins, containing 10 to 2,000 ppm of an active compound combination consisting of a 5-phenylcarbamoylbarbiturate (A) of the formula

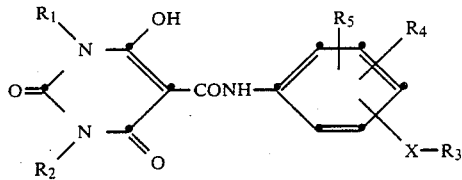

or a tautomeric form or a salt thereof, in which $R_1$ and $R_2$ independently of one another are $C_1-C_4$-alkyl, $C_4-C_6$-cycloalkyl, $C_2-C_4$-alkenyl, benzyl, phenyl or phenyl which is substituted by 1 to 3 substitutents belonging to the group comprising halogen, $C_1-C_4$-alkyl, $C_1-C_4$-alkoxy and nitro, $R_3$ is $C_1-C_4$-halogenoalkyl, phenyl or phenyl which is substituted by 1–3 substituents belonging to the group comprising $C_1-C_4$-halogenoalkyl, nitro, halogen and $C_1-C_4$-alkyl, $R_4$ and $R_5$ independently of one another are hydrogen, halogen, $C_1-C_4$-halogenoalkyl, $C_1-C_4$-alkyl, $C_2-C_4$-alkenyl, $C_3-C_6$ cycloalkyl, methoxy or nitro and X is oxygen or sulfur, it being also possible for $X-R_3$, together with $R_4$ and $R_5$ in the ortho-position, to be the group $-O-CF_2-O-CF_2-$, and (B) a synthetic pyrethroid.

* * * * *

UNITED STATES PATENT AND TRADEMARK OFFICE
CERTIFICATE OF CORRECTION

PATENT NO. : 4,503,100
DATED : March 5, 1985
INVENTOR(S) : Bernardo de Sousa et al.

It is certified that error appears in the above-identified patent and that said Letters Patent is hereby corrected as shown below:

Claim 2, Column 32, Line 43 should read--

A composition of claim 1, which contains, as--. delete -the-

Claim 5, Column 32, Lines 66-67 should read--

A composition of claim 1, which contains, as component (A), a compound of the formula in which X is --.

Claim 6, Column 33, Lines 1-2 should read--

A composition of claim 1, which contains, as component (A), a compound of the formula in which X is --.

Claim 13, Column 35, Line 53 should read--

$R_4$ or $R_5$ in the ortho-position, to be the group --.

Claim 21, Column 36, Line 63 should read--

$R_4$ or $R_5$ in the ortho-position, to be the group --.

Signed and Sealed this

First Day of October 1985

[SEAL]

Attest:

DONALD J. QUIGG

Attesting Officer

Commissioner of Patents and Trademarks—Designate